(12) United States Patent
Pickford et al.

(10) Patent No.: US 9,011,665 B2
(45) Date of Patent: Apr. 21, 2015

(54) METAL IMPLANTS

(75) Inventors: Martin Edward Lee Pickford, Southampton (GB); David Richard Lewis, Abingdon (GB); Andrew Derek Turner, Abingdon (GB)

(73) Assignee: Accentus Medical Limited, Didcot (GB)

(*) Notice: Subject to any disclaimer, the term of this patent is extended or adjusted under 35 U.S.C. 154(b) by 1083 days.

(21) Appl. No.: 10/591,793

(22) PCT Filed: Mar. 3, 2005

(86) PCT No.: PCT/GB2005/000645
§ 371 (c)(1),
(2), (4) Date: Sep. 6, 2006

(87) PCT Pub. No.: WO2005/087982
PCT Pub. Date: Sep. 22, 2005

(65) Prior Publication Data
US 2007/0181221 A1    Aug. 9, 2007

(30) Foreign Application Priority Data
Mar. 13, 2004   (GB) .................................. 0405680.0

(51) Int. Cl.
*A61L 27/06* (2006.01)
*A61L 27/30* (2006.01)
*A61L 27/32* (2006.01)
(Continued)

(52) U.S. Cl.
CPC .................. *A61L 27/32* (2013.01); *C25D 11/26* (2013.01); *C23C 28/042* (2013.01); *A61L 27/047* (2013.01); *A61L 27/06* (2013.01); *A61L 27/306* (2013.01); *A61L 27/54* (2013.01); *A61L 27/56* (2013.01); *A61L 2300/104* (2013.01); *A61L 2300/404* (2013.01); *A61L 2400/18* (2013.01)

(58) Field of Classification Search
USPC ................................... 205/200, 322
See application file for complete search history.

(56) References Cited

U.S. PATENT DOCUMENTS

| 4,027,393 A | 6/1977 | Ellis |
| 4,263,681 A | 4/1981 | Notton |

(Continued)

FOREIGN PATENT DOCUMENTS

| AU | 731730 B2 | 4/2001 |
| AU | 731732 B2 | 4/2001 |

(Continued)

OTHER PUBLICATIONS

T. Shibata et al, "The effect of temperature on the growth of anodic oxide film on titanium", Corrosion Science, vol. 37, No. 1, pp. 133-144, 1995.*

(Continued)

*Primary Examiner* — James Lin
*Assistant Examiner* — William Leader
(74) *Attorney, Agent, or Firm* — Christensen O'Connor Johnson Kindness PLLC

(57) ABSTRACT

A metal implant for use in a surgical procedure is provided with a surface layer that is integral with the metal substrate, and which incorporates a biocidal material. The surface layer is grown by anodizing at a voltage between 50 and 150 V, and the biocidal material incorporated in it by ion exchange. This produces a significantly harder surface than anodizing at low voltage, and generates pits containing ion-absorbing material.

10 Claims, 1 Drawing Sheet

(51) Int. Cl.
  *A61L 27/54* (2006.01)
  *C23C 28/04* (2006.01)
  *C25D 11/26* (2006.01)
  *A61L 27/04* (2006.01)
  *A61L 27/56* (2006.01)

(56) References Cited

U.S. PATENT DOCUMENTS

| | | | |
|---|---|---|---|
| 4,336,617 A | 6/1982 | Shikita | |
| 4,784,160 A | 11/1988 | Szilagyi | |
| 4,806,218 A | 2/1989 | Hemminger et al. | |
| 4,813,965 A | 3/1989 | Roberts | |
| 4,818,572 A | 4/1989 | Shimamune et al. | |
| 4,846,837 A | 7/1989 | Kurze et al. | |
| 4,938,409 A | 7/1990 | Roberts | |
| 5,032,129 A | 7/1991 | Kurze et al. | |
| 5,132,003 A | 7/1992 | Mitani | |
| 5,185,075 A | 2/1993 | Rosenberg | |
| 5,211,663 A | 5/1993 | Kovacs et al. | |
| 5,211,832 A * | 5/1993 | Cooper et al. | 205/322 |
| 5,310,464 A | 5/1994 | Redepenning | |
| 5,454,886 A | 10/1995 | Burrell | |
| 5,468,562 A | 11/1995 | Farivar et al. | |
| 5,478,237 A | 12/1995 | Ishizawa | |
| 5,482,731 A | 1/1996 | Vargas-Gutierrez | |
| 5,486,231 A * | 1/1996 | Dulaney | 106/243 |
| 5,492,763 A | 2/1996 | Barry | |
| 5,503,704 A | 4/1996 | Bower et al. | |
| 5,520,664 A | 5/1996 | Bricault, Jr. et al. | |
| 5,612,049 A | 3/1997 | Li et al. | |
| 5,695,857 A | 12/1997 | Burrell | |
| 5,723,038 A | 3/1998 | Scharnweber et al. | |
| 5,753,251 A | 5/1998 | Burrell et al. | |
| 5,753,322 A | 5/1998 | Yamaguchi et al. | |
| 5,770,255 A | 6/1998 | Burrell | |
| 5,833,463 A | 11/1998 | Hurson | |
| 5,837,275 A | 11/1998 | Burrell et al. | |
| 5,855,612 A | 1/1999 | Ohthuki et al. | |
| 5,958,440 A | 9/1999 | Burrell et al. | |
| 5,985,308 A | 11/1999 | Burrell et al. | |
| 6,017,553 A | 1/2000 | Burrell et al. | |
| 6,066,392 A | 5/2000 | Hisamoto et al. | |
| 6,113,636 A | 9/2000 | Ogle | |
| 6,180,162 B1 | 1/2001 | Shigeru et al. | |
| 6,190,407 B1 | 2/2001 | Ogle et al. | |
| 6,267,782 B1 * | 7/2001 | Ogle et al. | 623/1.1 |
| 6,322,588 B1 | 11/2001 | Ogle et al. | |
| 6,361,567 B1 | 3/2002 | Dearnaley | |
| 6,365,220 B1 | 4/2002 | Burrell | |
| 6,482,444 B1 | 11/2002 | Bellantone et al. | |
| 6,509,057 B2 | 1/2003 | Shigeru et al. | |
| 6,544,288 B2 | 4/2003 | Osaka et al. | |
| 6,582,715 B1 | 6/2003 | Barry et al. | |
| 6,663,634 B2 | 12/2003 | Ahrens | |
| 6,689,170 B1 | 2/2004 | Larsson et al. | |
| 6,719,987 B2 | 4/2004 | Burrell et al. | |
| 6,866,859 B2 | 3/2005 | Trogolo et al. | |
| 6,913,617 B1 | 7/2005 | Reiss | |
| 7,029,566 B2 | 4/2006 | Yen | |
| 7,048,541 B2 | 5/2006 | Hall et al. | |
| 7,192,445 B2 | 3/2007 | Ellingsen et al. | |
| 7,452,566 B2 | 11/2008 | Sul | |
| 7,488,343 B2 * | 2/2009 | O'Brien et al. | 623/1.15 |
| 2002/0099449 A1 | 7/2002 | Speitling | |
| 2003/0045941 A1 | 3/2003 | Lewallen | |
| 2004/0121290 A1 * | 6/2004 | Minevski et al. | 433/201.1 |
| 2004/0161473 A1 | 8/2004 | Joshi | |
| 2004/0234604 A1 | 11/2004 | Mecking et al. | |
| 2004/0236338 A1 | 11/2004 | Hall | |
| 2005/0177248 A1 | 8/2005 | Hall | |
| 2005/0221259 A1 | 10/2005 | Anderson | |
| 2006/0035039 A1 | 2/2006 | Ylitalo et al. | |
| 2006/0198903 A1 | 9/2006 | Storey et al. | |
| 2007/0187253 A1 | 8/2007 | Gilbert et al. | |
| 2008/0011613 A1 | 1/2008 | Wang | |
| 2009/0035722 A1 | 2/2009 | Balasundaram et al. | |
| 2009/0093881 A1 | 4/2009 | Bandyopadhyay et al. | |
| 2009/0104242 A1 | 4/2009 | Karlinsey | |
| 2009/0124984 A1 | 5/2009 | Hanawa | |
| 2009/0155335 A1 | 6/2009 | O'Shaughnessey et al. | |
| 2009/0164027 A1 | 6/2009 | Zipprich | |
| 2009/0198344 A1 | 8/2009 | Prentice et al. | |
| 2009/0204213 A1 | 8/2009 | Liao et al. | |

FOREIGN PATENT DOCUMENTS

| | | |
|---|---|---|
| BG | 62807 B1 | 8/2000 |
| CA | 2136456 C | 6/1999 |
| EP | 0257923 A2 | 3/1988 |
| EP | 00257923 B1 | 1/1992 |
| EP | 0555004 A1 | 8/1993 |
| EP | 0761182 A3 | 3/1998 |
| EP | 00875146 B1 | 7/2002 |
| EP | 1207220 B1 | 1/2008 |
| GB | 2072514 A | 10/1981 |
| GB | 2073024 A | 10/1981 |
| GB | 2073024 A | 10/1981 |
| GB | 2136448 | 9/1984 |
| JP | 58-167798 A1 | 10/1983 |
| JP | 62-182298 A1 | 8/1987 |
| JP | 10-168597 A1 | 6/1998 |
| JP | 10158889 | 6/1998 |
| JP | 10168598 | 6/1998 |
| JP | 11181596 | 7/1999 |
| JP | 11-209895 A1 | 8/1999 |
| JP | 11229186 | 8/1999 |
| JP | 11236699 | 8/1999 |
| JP | 11-302570 A1 | 11/1999 |
| JP | 11343592 | 12/1999 |
| JP | 2005287985 A | 10/2005 |
| JP | 2005287985 A | 10/2005 |
| KR | 10-0910064 B1 | 7/2009 |
| RU | 2167526 C2 | 5/2001 |
| SI | 875146 T1 | 12/2002 |
| WO | WO 81/02667 A1 | 10/1981 |
| WO | WO 81/02668 A1 | 10/1981 |
| WO | WO 92/11043 A1 | 7/1992 |
| WO | WO 93/07924 A1 | 4/1993 |
| WO | WO 95/13704 A1 | 5/1995 |
| WO | WO 95/18637 A1 | 7/1995 |
| WO | 98/51231 | 11/1998 |
| WO | 99/01089 A1 | 1/1999 |
| WO | WO 99/01089 A1 | 1/1999 |
| WO | WO 99/26666 A2 | 6/1999 |
| WO | WO 00/45724 A1 | 8/2000 |
| WO | 00/51659 A1 | 9/2000 |
| WO | WO 00/51659 A1 | 9/2000 |
| WO | WO 00/64505 A1 | 11/2000 |
| WO | 00/72777 | 12/2000 |
| WO | WO 01/12246 A1 | 2/2001 |
| WO | 02/096475 | 12/2002 |
| WO | WO 02/096475 A1 | 12/2002 |
| WO | 03/003938 | 1/2003 |
| WO | WO 03/039609 A1 | 5/2003 |
| WO | 03/089023 | 10/2003 |
| WO | WO 03/089023 A1 | 10/2003 |
| WO | WO 03/094774 | 11/2003 |
| WO | WO 2004/002543 A1 | 1/2004 |
| WO | WO 2005/087982 | 9/2005 |
| WO | WO 2006/004686 A2 | 1/2006 |
| WO | WO 2006/058906 A1 | 6/2006 |
| WO | WO 2006/104644 | 10/2006 |
| WO | WO 2006/104644 A2 | 10/2006 |
| WO | WO 2007/050327 A2 | 5/2007 |
| WO | WO 2007/144667 A2 | 12/2007 |
| WO | WO 2008/096160 A2 | 8/2008 |
| WO | WO 2009/044203 A1 | 4/2009 |
| WO | WO 2009/100792 A2 | 8/2009 |
| WO | WO 2009/100792 A3 | 8/2009 |

(56) References Cited

FOREIGN PATENT DOCUMENTS

OTHER PUBLICATIONS

T. Shibata et al, "The effect of film formation conditions on the structure and composition of anodic oxide films on titanium", Corrosion Science, vol. 37, No. 2, pp. 253-270, 1995.*
X. Zhu et al, "Anodic oxide films containing Ca and P of titanium biomaterial", Biomaterials, 22 (2001) 2199-2206.*
Shirkhanzadeh et al., "Bioactive delivery systems for the slow release of antibiotics: incorporation of Ag+ ions into micro-porous hydroxyapatite coatings", Materials Letters 24, Jun. 1995, pp. 7-12.
PCT International Search Report and Written Opinion for International Application No. PCT/GB2008/050894 dated Dec. 18, 2008.
GB Search Report for Application No. GB0818043.2 dated May 22, 2009.
Afshar, "Evaluation of electrical breakdown of anodic films on titanium in phosphate-base solutions", 2004.
Aladjem, "Review anodic oxidation of titanium and its alloys", 1973.
Aerospace Material Spec. (AMS 2487A), "Anodic treatment of titanium alloys solution pH 12.4 maximum", 1993-2006.
Aerospace Material Spec. (AMS 2488D), "Anodic treatment—titanium and titanium alloys solution pH 13 or higher", 1977-2006.
Chen, "Surface chemistry of TiCl4 on W(100)", 1996.
Chi, "Antibacterial activity of anodized aluminum with deposited silver", 2002.
Disegi, "Anodizing treatments for titanium implants", 1997.
Dunn, "Anodized layers on titanium and titanium alloy orthopedic materials for antimicrobial activity applications", 1992.
Dunn, "Formation and characterization of anodized layers on CP Ti and Ti-6Al-4OV", 1992.
Dunn, "Gentamicin sulfate attachment and release from anodized Ti-6Al-4V orthopedic materials", 2004.
Edwards, "Coating and surface treatment systems for metals", 1997.
Kawashita, "Bonelike apatite formation on anodically oxidized titanium metal in simulated body fluid", 2004.
Khadiri, "Characterization of titanium oxide thin films anodically grown in phosphoric acid", 2004.
Kokubo, "Novel bioactive materials with different mechanical properties", 2003.
Kurze et al., "Application fields of ANOF layers and composites", 1986.
Li et al., "Calcium phosphate formulation within sol-gel prepared titanium in vitro and in vivo", 1993.
Li et al., "The role of hydrated silica, titania and alumina in inducing apatite on implants", 1994.
Liu, "Surface modification of titanium, titanium alloys, and related materials for biomedical applications", 2004.
Marchenoir, "Study of porous layers formed by anodic oxidation of titanium under high voltage" (French), 1980.
Marchenoir, "Study of porous layers formed by anodic oxidation of titanium under high voltage" (English translation), 1980.
Martini, "Detachment of titanium & fluorhydroxypatite particles", 2003.
Necula, "In vitro antibacterial >activity of porous TiO2—Ag composite layers against methicillin-resistant *Staphylococcus aureus*", 2009.
Olier, "Influence of the preparation conditions of titanium surfaces on the formation of anodic oxide layers" (French), 1980.
Olier, "Influence of the preparation conditions of titanium surfaces on the formation of anodic oxide layers" (English translation), 1980.
Schierholz, "Efficacy of silver-coated medical devices", 1998.
Schreckenbach, "Characterization of anodic spark-converted titanium surfaces for biomedical applications", 1999.
Shirkhanzadeh, "Nanoporous alkoxy-derived titanium oxide coating", 1998.
Souza, "EIS characterization of Ti anodic oxide porous films formed using modulated potential", 2007.
Suzuki et al., "Surface treatment of titanium (part 4) in vitro biocompatibility of titanium treated by the anodic spark oxidation", 1991.
Takasaki, "Elution of silver ions from A-type zeolite supporting silver ions in aqueous solutions" (Japanese), 1996.
Takasaki, "Elution of silver ions from A-type zeolite supporting silver ions in aqueous solutions" (English translation), 1996.
Tsukada, "Low-temperature electrochemical systhesis of ZrO2 films on zirconium substrates", 1997.
Xie, "Improvement of surface bioactivity on titanium by water and hydrogen plasma immersion ion implantation", 2005.
Yang, "Preparation of bioactive titanium metal via anodic oxidation treatment", 2004.
Yoshinari, "Influence of surface modifications to titanium on antibacterial activity in vitro", 2001.
Yu, "Synthesis and characterization of phoshated meso porous titanium dioxide with photocatalytic activity", 2003.
Yue, "Bioactive titanium metal surfaces with antimicrobial properties prepared by anodic oxidation treatment", 2009.
Wertz and Cook, "Phosphoric Acid Solutions. I: Molecular Association in a 57.8 Molal Aqueous Solution", Journal of Solution Chemistry, vol. 14, No. 1, 1985, pp. 41-48.
English language abstract of JP10158889, Jun. 16, 1998.
English language abstract of JP10168598, Jun. 23, 1998.
English language abstract of JP11181596, Jul. 6, 1999.
English language abstract of JP11229186, Aug. 24, 1999.
English language abstract of JP11236699, Aug. 31, 1999.
English language abstract of JP11343592, Dec. 14, 1999.
English language abstract of JP2005287985, Oct. 20, 2005.

* cited by examiner

METAL IMPLANTS

This invention relates to metal implants for use in surgical procedures, and in particular to the introduction of a biocidal material into such implants to suppress or control infection.

Various surgical procedures require the use of implants. For example cancerous bone may be removed, in prosthetic surgery, to be replaced by a metal implant. Such an implant may for example be of titanium alloy, which is very strong and relatively light. To ensure a hard-wearing surface the provision of a titanium nitride coating has been suggested. There is furthermore a risk of introducing infection when implanting such metal implants, and it has been suggested that metallic silver might be electroplated onto metal implants, the silver being a biocidal material that can control infection without causing toxic effects to the patient. However such coatings, whether of titanium nitride or silver, may be undercut due to corrosion from body fluids, so that the coating may detach from the implant, which may can increase wear and cause tissue damage. WO 03/089023 describes a way of pretreating an implant by anodising at 10 V to form a phosphate layer, and then incorporating biocidal silver ions in this layer by ion exchange. A way of making a significantly improved layer has now been found.

According to the present invention there is provided a method of treating a titanium metal implant for use in a surgical procedure, so as to form a surface layer that is integral with the metal substrate and which incorporates a biocidal material, wherein the method comprises anodising the implant at a voltage above 50 V for a period of at least 30 min, so as to generate a surface layer, and then performing ion exchange so as to incorporate ions of a biocidal metal into the surface layer.

The biocidal material should preferably be effective for at least 6 weeks, preferably for up to 6 months after surgery, and the release rate should be low to avoid toxic effects on body cells. Furthermore the total quantity of biocidal material is preferably also limited to minimize any toxic effects. Performing the anodising at a voltage above 50 V has two effects: it initially generates a dense hard surface layer whose thickness is primarily determined by the voltage, and it then generates shallow pits in the surface which are filled with a somewhat softer and more porous material. The absorption of biocidal metal ions is primarily into the material within the shallow pits, so that the total quantity of biocidal material and its release rate can be controlled by controlling the magnitude of the anodising voltage and its duration, so as to control the number and size of the shallow pits. The anodizing might be carried out at a voltage as high as 500 V or 750 V, but more usually is performed between 50 V and 150 V. The duration may be up to 24 hours, but preferably no more than 12 hours, for example 2 hours or 6 hours.

It is also desirable if the surface is highly polished before production of the surface layer. This may for example be achieved by electropolishing. One benefit of performing the anodising at a voltage in this significantly higher range is that the surface finish is not deleteriously affected; if the surface is polished before anodising so as to be shiny, then it will remain shiny after the high-voltage anodising step. This is in contrast to the effect of low voltage anodising, which generates a milky or matt appearance at the surface.

In principle, a range of different materials may be used for the biocidal material. Gold, platinum and palladium would be potentially suitable, although expensive; silver is preferable as it is not particularly soluble in body fluids due to the presence of chloride ions and the low solubility of silver chloride. Other elements such as copper, tin, antimony, lead, bismuth and zinc might be used as ions combined into the surface layer. The rate of release would be controlled, in this case, primarily by the strength of the absorption of the metal ions in the layer.

The term titanium metal implant refers to an implant of a metal that is predominantly titanium, preferably at least 75% titanium by weight. The invention is applicable to prosthetic implants that are made of pure titanium, or a titanium alloy. The standard alloy for this purpose is titanium 90% with 6% aluminium and 4% vanadium (British standard 7252).

Preferably the implant is initially polished to provide a very smooth surface. Titanium alloy can be electro-polished using acetic acid, or a mixture of nitric and hydrofluoric acids. Alternatively the implants might be subjected to a combination of anodic passivation with mechanical polishing, which may be referred to as electrolinishing, this process removing the oxide that protects surface roughness, the surface at that point then being electrochemically re-passivated, so producing a mirror-smooth finish. Various electrolytes are suitable for this purpose, including nitric acid mixed with sulphuric acid, sodium hydroxide, sodium phosphate, or sodium hydroxide mixed with sodium nitrate.

After polishing the surface of the metal, surface conversion can take place. A layer of metal oxide or phosphate is formed by anodising in a suitable electrolyte, so that the oxide or phosphate layer builds up at the surface of the metal, as described above. Biocidal metal ions can then be absorbed from an aqueous salt solution into the oxide or phosphate matrix, for example the ions Ag+ or Cu++. Cations of palladium, platinum or even ruthenium could be absorbed in a similar way. If desired, deposited silver, platinum or palladium could then be converted to metal within the oxide or phosphate surface coating, this reduction being performed chemically or electrochemically or by light.

The invention will now be further and more particularly described, by way of example only, and with reference to the accompanying drawings in which.

A hip implant is made of titanium alloy (Ti/Al/V) The implant is cleaned ultrasonically using first acetone as the liquid phase, and then a 1 M aqueous solution of sodium hydroxide, and is then rinsed in de-ionised water. The surface is initially shiny, with a pale grey colour. The cleaned implant is then immersed in a stirred 12% (weight) solution of phosphoric acid, and is anodised for 2 hours at a maximum voltage of 100 V and a maximum current of 10 mA/cm$^2$, so as to form a surface coating of titanium oxide and phosphate. Within a couple of minutes a dense dielectric layer is formed on the surface, and the current then adopts a stable low value for the rest of the anodising period. The surface forms a hard surface layer which can have different coloured appearances due to optical interference effects; during the initial stage of anodising, the surface colour varies from purple/blue, through blue, green, yellow, orange, and then finally red. Anodising at 100 V produces a film thickness of about 0.14 μm (140 nm). The anodised implant is then rinsed in de-ionised water again.

The implant is then immersed in a stirred 0.1 M aqueous solution of silver nitrate, and left for 2 hours. As a result of ion exchange there is consequently some silver phosphate in the titanium phosphate coating. The implant is then ready to be implanted. During exposure to body fluids there will be a slow leaching of silver ions from the phosphate layer, so that any bacteria in the immediate vicinity of the implant are killed. Infection arising from the implant is therefore suppressed.

Figure 1:
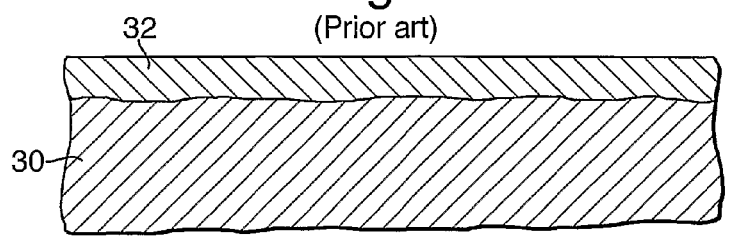
FIG. 1 shows a diagrammatic sectional view through part of the surface of an implant subjected to a low voltage anodising treatment.

Referring to FIG. 1, where anodising of a titanium implant 30 is performed at 10 V for 2 hours, the current falls to a low value over the first couple of minutes during anodising, but the current then rises again with the formation of a porous surface layer with 20 μm macropores and 1 μm micropores. This produces a porous high-surface-area layer 32 which is about 2 μm thick, of hydrous titanium oxide and phosphate. This is highly effective at absorbing silver ions, and can provide an initial silver capacity of about 70-100 μg/cm$^2$; this is well below the toxic level, but more than adequate to provide a biocidal effect.

Figure 2:
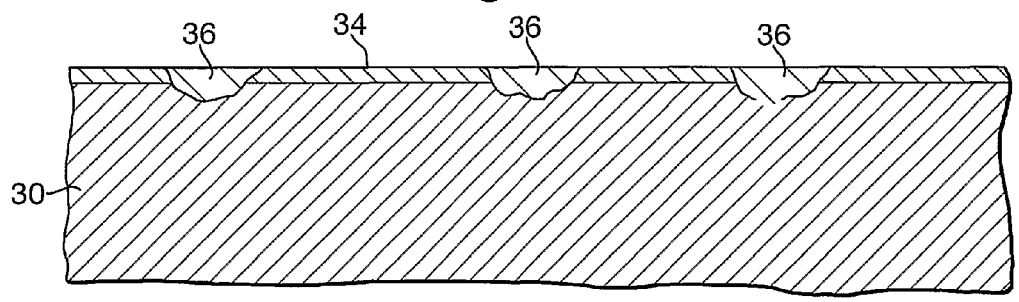
FIG. 2 shows a corresponding sectional view of an implant subjected to a high-voltage anodising treatment of the invention.

Referring to FIG. 2, where anodising is performed at a high voltage such as 100 V for 2 hours, as mentioned above the current initially falls to a low value, and then remains steady. The surface forms a hard anodised oxide layer 34 typically of thickness about 0.14 μm, but in which there are pits 36 typically of diameter about 5 μm and depth about 0.4 μm which are filled with titanium oxide as a result of hydrolysis from localised titanium dissolution. Such pits 36 are approximately circular in plan, and make up between 15 and 20% of the surface area. Surface analysis techniques have confirmed that, after ion exchange treatment, the absorbed silver is associated with the titanium oxide/phosphate phase at the surface; this is true for both the low voltage and the high-voltage anodising procedures. The high-voltage anodised surface absorbs silver to a small extent at the outer surface of the hard layer 34, and to a larger extent within the more porous material in the pits 36; overall there is somewhat less initial capacity for silver, typically about 9 μg/cm$^2$. This is still sufficient to provide the required biocidal effect.

Thus the effects of anodising at 100 V for 2 hours are to produce a hard and compact oxide layer whose thickness depends upon the voltage (the relationship being approximately 1.4 nm per volt) this film having a coloured appearance determined by the film thickness, and retaining the surface microstructure (e.g. polished finish). Furthermore the surface is pitted, with pits about 0.3 μm deep filled with hydrous titanium dioxide covering slightly less than a fifth of the surface. This can be loaded with silver at about 9 μg/cm$^2$.

Figure 3:
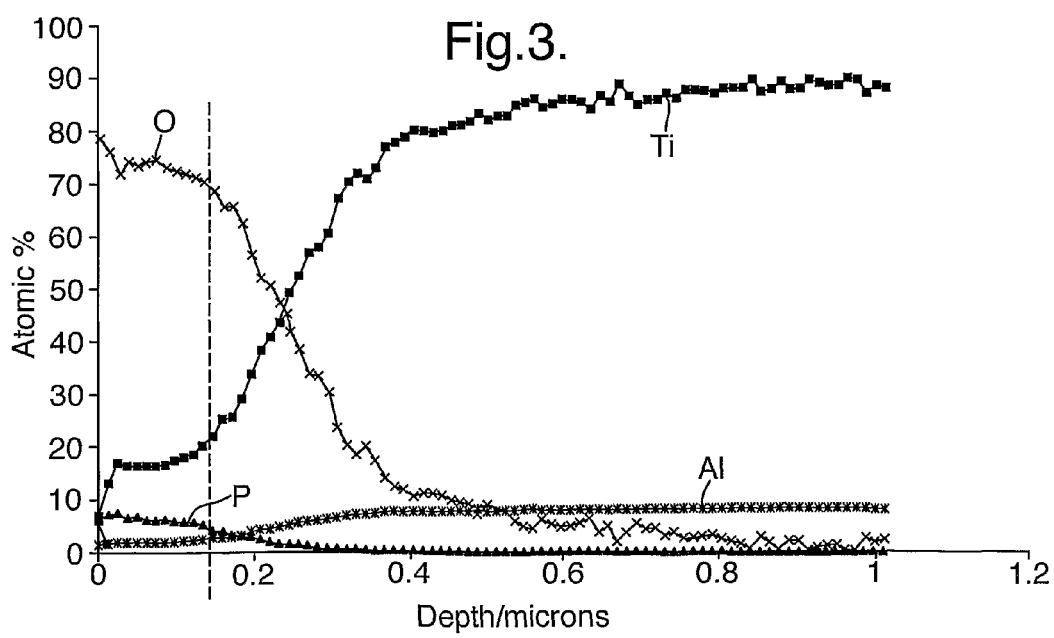
FIG. 3 shows the surface composition profile of a specimen treated as in FIG. 2, the profile being determined by secondary neutral mass spectrometry.

Measurements of the surface composition at different depths below the surface have been measured using secondary neutral mass spectrometry on a titanium alloy specimen treated as described above. The results are shown in FIG. 3, to which reference is now made. It will be observed that in the surface region, down to about 0.14 μm (marked by the broken line), the composition is about 73% oxygen and about 18% titanium, with phosphorus at about 6%; this corresponds to the hard surface layer 34. There is then a zone in which the titanium concentration increases and the oxygen concentration decreases, down to about 0.4 μm; this corresponds to the depths at which there are pits 36 containing titanium oxide. At greater depths the composition is evidently a titanium/aluminium alloy.

Measurements have also been made of the loss of silver from the surface of the anodised implant into a brine flowing over the surface (at a linear velocity of about 0.7 ml cm$^{-2}$ h$^{-1}$). The initial rate of silver release over the first 24 hours is about 0.1 μg cm$^{-2}$ h$^{-1}$, the release rate then gradually falling over the next 24 hours to about half that value, then remaining steady for another 48 hours, before decreasing again. But throughout this period the concentration of silver in the leaching brine was sufficient to be biocidal.

The silver capacity can be adjusted in three ways. It may be changed by changing the number of pits, and this can be either by changing the voltage, or by changing the concentration of pitting agents (such as chloride or fluoride ions) which are present as impurities in the phosphate electrolyte. For example the concentration of such monovalent ions can be decreased by a selective anion exchange treatment; or their concentration could be increased by adding appropriate acids. For example the concentration of chloride ions might be increased by adding NaCl or hydrochloric acid to the phosphoric acid electrolyte, preferably such that the chloride ion concentration is no more than 500 ppm, more preferably no more than 50 ppm. Alternatively the pits might be grown to larger depths and diameters; this may be achieved by carrying out the anodising for a longer period of time.

It may also be appropriate to change the current density.

By anodising at a higher voltage the thickness of the hard oxide layer can be increased, for example being about 0.7 μm at 500 V. Once this layer has been formed, as indicated by the decrease in the current, the voltage might be changed. During this second stage the pits are formed, and gradually grow in size, and this may be carried out at a lower voltage.

It will be appreciated that the invention is also applicable to implants which are at least partly made of porous titanium, as the high-voltage anodising process is effective within the pores. This can lead to significantly higher loading of silver per unit volume of implant, because of the much larger surface area.

The electrical connection to the implant, so that anodising can be performed, may for example be through a titanium wire spot-welded onto the implant. Alternatively a blind hole may be drilled into the implant, and electrical connection made by a screw connector in this hole, a sealant (for example silicone) preventing electrolyte access to the contact area. Exposed parts of the connector can be protected from anodisation for example by a PTFE insulating tape. After the anodising process, the connector would be removed, and the hole could be filled by a bio-compatible plug, for example of anodised titanium, or of a polymer.

The invention claimed is:

1. A titanium metal implant comprising a metal substrate for use in a surgical procedure, said implant having a mirror finish surface layer integral with said metal substrate and incorporating a biocidal metal material, said implant comprising as said surface layer an anodized hard layer including pits in said hard layer, the hard layer having a thickness between 0.07 microns and 0.7 microns and having a coloured appearance determined by the thickness, said pits being filled with a softer and more porous material than the hard layer, wherein the softer and more porous material comprises hydrous titanium dioxide, and wherein the surface layer comprises a surface area, and wherein said pits are of a diameter about 5 microns and said pits occupy between 15 and 20% of the surface area of the surface layer, said pits extending through said hard layer into said metal substrate, said hard layer and said pits including ions of said biocidal metal material as a result of ion exchange, with said more porous material in the pits having absorbed biocidal metal material to a larger extent than said hard layer, and wherein a phosphate matrix is present at said surface layer of said metal substrate, and wherein the phosphate matrix comprises biocidal metal ions.

2. A titanium metal implant according to claim 1, wherein titanium is present in said substrate at at least 75% by weight.

3. A titanium metal implant according to claim 2, wherein the titanium is present as pure titanium or as a titanium alloy.

4. A titanium metal implant according to claim 1, wherein the biocidal metal ions are selected from the group consisting of: silver, gold, platinum, ruthenium and palladium.

5. A titanium metal implant according to claim 1, wherein the hard layer is 0.14 micrometers thick.

6. A titanium metal implant according to claim 5, wherein the pits in the hard layer have a depth of approximately 0.4 micrometers.

7. A titanium metal implant according to claim 1, wherein other elements are present in said surface layer, selected from the group consisting of: copper, tin, antimony, lead, bismuth and zinc.

8. A method of treating a titanium metal implant comprised of a metal substrate for use in a surgical procedure, said method including the steps of polishing a surface of the implant to obtain a mirror finish, anodising the implant for forming a surface layer integral with said metal substrate, rinsing the anodised implant, and then performing ion exchange so as to incorporate ions of a biocidal metal into the surface layer, characterised in that said method comprises anodising the implant for a period of more than 30 minutes so as to generate the surface layer, wherein the anodising comprises applying a voltage between 50 volts and 150 volts to said surface of said implant in an electrolyte comprising phosphoric acid of concentration between 5% and 20% by weight, wherein said surface retains a mirror finish after said anodising step, and wherein the anodising is performed for sufficient time to initially generate a dense hard surface layer and then also to generate shallow pits in the surface layer which are filled with a somewhat softer and more porous material comprising hydrous titanium dioxide, wherein the surface layer comprises a surface area, and wherein said pits are of a diameter about 5 microns and occupy between 15% and 20% of the surface area of the surface layer, said pits extending through said hard layer into said metal substrate, wherein, in the ion exchange step, said more porous material in the pits absorbs biocidal metal to a larger extent than said hard layer.

9. A method as claimed in claim 8, wherein said biocidal metal is silver.

10. A method as claimed in claim 8, wherein chloride ions are added to the electrolyte, so the electrolyte comprises chloride ions at a concentration no more than 500 ppm.

\* \* \* \* \*